United States Patent
Kitazawa et al.

(10) Patent No.: US 7,543,482 B2
(45) Date of Patent: Jun. 9, 2009

(54) CARBON THIN LINE PROBE

(75) Inventors: Masashi Kitazawa, Ina (JP); Masaki Tanemura, Owariasahi (JP); Junya Tanaka, Aichi (JP); Tatsuhiko Okita, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/710,974

(22) Filed: Feb. 27, 2007

(65) Prior Publication Data

US 2007/0204681 A1  Sep. 6, 2007

(30) Foreign Application Priority Data

Mar. 3, 2006  (JP)  ............................ 2006-057371

(51) Int. Cl.
*G12B 21/08* (2006.01)
*B82B 1/00* (2006.01)

(52) U.S. Cl. .................. 73/105; 73/866.5; 977/860; 977/863; 977/875; 977/876; 977/879

(58) Field of Classification Search ............... 73/105, 73/866.5; 977/742, 745, 762, 860, 863, 875, 977/876, 879, 953
See application file for complete search history.

(56) References Cited

U.S. PATENT DOCUMENTS

| 7,112,315 B2 * | 9/2006 | Kiang ..................... 423/447.1 |
| 2003/0095356 A1 | 5/2003 | Nakayama et al. |
| 2004/0265209 A1 * | 12/2004 | Colbert et al. ........... 423/447.1 |
| 2007/0087436 A1 | 4/2007 | Miyawaki et al. |

FOREIGN PATENT DOCUMENTS

| EP | 0 483 579 A2 | 10/1991 |
| EP | 1 278 056 A1 | 1/2003 |

(Continued)

OTHER PUBLICATIONS

Guerret-Plécourt, C. et al., "Relation Between Metal Electronic Structure and Morphology of Metal Compounds Inside Carbon Nanotubes", Nature, vol. 372, Dec. 22, 1994, pp. 761-765.*

(Continued)

*Primary Examiner*—Daniel S Larkin
(74) *Attorney, Agent, or Firm*—Westerman, Hattori, Daniels & Adrian, LLP.

(57) ABSTRACT

A carbon thin line probe having a carbon thin line selectively formed at a projection-like terminal end portion thereof by means of an irradiation of high-energy beam, the carbon thin line internally containing a metal. Thereby achieved is a carbon thin line probe suitable for example for the probe of SPM cantilever, which has a high aspect ratio and high durability and reliability, capability of batch processing based on a simple manufacturing method, and to which magnetic characteristic can be imparted.

1 Claim, 5 Drawing Sheets

FOREIGN PATENT DOCUMENTS

| | | |
|---|---|---|
| EP | 1 557 843 A2 | 7/2005 |
| EP | 1 742 034 A1 | 1/2007 |
| JP | 2000321292 A | 11/2000 |
| JP | 2003-90788 A | 3/2003 |
| WO | 2004/038430 A2 | 5/2004 |
| WO | 2004/092369 A1 | 10/2004 |
| WO | 2005/103648 A1 | 11/2005 |

OTHER PUBLICATIONS

Stevens, R.M.D. et al., "Carbon Nanotubes as Probes for Atomic Force Microscopy", Nanotechnology, vol. 11, 2000, pp. 1-5.*

Zhang, Z.L. et al., "Filling of Single-Walled Carbon Nanotubes with Silver", Journal of Material Research, vol. 15., No. 12, Dec. 2000, pp. 2658-2661.*

Search Report dated Jan. 15, 2008, issued in corresponding European Application No. 07103380.7.

* cited by examiner

CARBON THIN LINE PROBE

This application claims benefit of Japanese Patent Application No.2006-57371 filed in Japan on Mar. 3, 2006, the contents of which are incorporated by this reference.

BACKGROUND OF THE INVENTION

The present invention relates to carbon thin line probes, and more particularly relates to a carbon thin line probe internally containing a metal so as to be suitable for the probe of a scanning probe microscope (SPM) or probe of a microinjector.

The scanning probe microscopes (SPM) have measuring resolutions of atomic order and are used in various fields, such as in measurements of the surface configuration of a substance. With recent SPM, probes having high aspect ratio are demanded, since there are an increasing requirement for high resolution and requirement for measuring those portions such as the interior of a trench that has not been reached by a probe heretofore.

Also in recent years, researches are widely conducted on carbon nanotube (hereinafter referred to as CNT), whereby CNT having a high aspect ratio of several nanometers to several- ten nanometers in diameter and several μm to several-ten μm in length can now be formed using thermal decomposition or arc discharge. These CNT's are known to be almost completely graphitized and have bonding states equal to or exceeding that of a diamond which has a high level of hardness and thus are exceptionally excellent in mechanical strength characteristics.

Under these circumstances, use of CNT having a high aspect ratio with excellent mechanical strength as a probe of SPM cantilever draws attention. Japanese Patent Application Laid-Open 2000-321292 for example discloses CNT having an ultrafine particle of metal fixed to its terminal end and a method for adhering/fixing such CNT to a probe terminal end portion of the cantilever of atomic force microscope (AFM).

Shown in FIGS. 1A to 1D are manufacturing processing drawings for explaining a manufacturing method of CNT where the metal ultrafine particle disclosed in the above publication is fixed to its terminal end. First as shown in FIG. 1A, a silicon substrate 101 having iron oxide on its front surface is prepared. Next as shown in FIG. 1B, an Ni metal film 102 is formed on the front surface of the silicon substrate 101, and it is placed in a high vacuum cylindrical container and heated in a He gas atmosphere. The Ni metal film is thereby changed into ultrafine particles 103 as shown in FIG. 1C. Subsequently, by causing a flow of $C_6H_6$ gas while maintaining a vacuum, a CNT 104 is formed on the lower end of a Ni ultrafine particle 103 by means of dehydro catalytic reaction. Thus, CNT 105 with the ultrafine particle of Ni is formed as shown in FIG. 1D.

FIG. 2 illustrates a method also disclosed in the above publication for fixing the CNT with the ultrafine particle to an AFM cantilever probe. In this fixing method, a DC electric field resulting from a DC power supply 113 is applied between a silicon substrate 111 with the CNT having the ultrafine particle 117 formed thereon and AFM cantilever 112, and the CNT having the ultrafine particle 117 is caused to leap and transit so as to be fixed to a cantilever probe 115 by means of electrostatic force. In this case, adjustment is made so that ultrafine particle 116 protrudes beyond the terminal end with an axis 114 of CNT 117 being substantially vertical to the cantilever 112, and a proximal end portion 117a thereof is bonded to the probe 115. The CNT having the ultrafine particle 117 is thus fixed to cantilever 112, this operation being performed while observation is directly made through an electron microscope.

In addition, the above publication discloses another method where a proximal end portion of the CNT, when irradiated by an electron beam, is denatured and becomes a fusion bonding portion so that it is fixed by means of thermal fusion bonding to the probe of cantilever. Also disclosed is a method where an electric current is caused to flow between CNT and the cantilever so that a proximal end portion thereof is denatured and made into a fusion bonding portion to be fixed. It furthermore discloses a method in which, when an electron beam is irradiated onto the vicinity of CNT at the interior of an electron microscope where a carbon compound occurs as impurity, a coating film consisting of a carbon coat is deposited over a proximal end portion of CNT whereby CNT is firmly fixed to the probe through the coating film.

Since the ultrafine particle of thus constructed CNT having ultrafine particle can be used as a sensor part for observing a surface of substance, it is possible to achieve CNT having ultrafine particle capable of high precision measurements without being affected for example by variance in the structure of CNT itself. Further, since magnetism on a surface of substance to be measured is detected if a ferromagnetic metal fine particle, such as Fe, Ni, or Co, is used as the ultrafine particle, it is possible to read a magnetic surface structure of the substance to be measured.

SUMMARY OF THE INVENTION

The object of the present invention is to provide a carbon thin line probe for example of CNT which has a high aspect ratio and high durability and reliability, capability of batch processing based on a simple manufacturing method, and to which magnetic characteristic can be imparted.

To achieve the above object, there is provided in accordance with a first aspect of the invention a carbon thin line probe having a carbon thin line selectively formed at a projection-like terminal end portion thereof by means of an irradiation of a high-energy beam. The carbon thin line internally contains a metal.

In a second aspect of the invention, the internally contained metal of the carbon thin line probe according to the first aspect is formed through the entire portion of the carbon thin line.

In a third aspect of the invention, the internally contained metal of the carbon thin line probe according to the first aspect is formed at a terminal end portion or proximal end portion of the carbon thin line.

In a fourth aspect of the invention, the internally contained metal of the carbon thin line probe according to the second or third aspect is formed so as to uniformly fill and be integral with an interior of the carbon thin line.

In a fifth aspect of the invention, the internally contained metal of the carbon thin line probe according to the second or third aspect is formed so as to be scattered through an interior of the carbon thin line.

In a sixth aspect of the invention, the internally contained metal of the carbon thin line probe according to any one of the first to fifth aspects is a metal having a magnetic characteristic or its alloy.

In a seventh aspect of the invention, at least a portion of the carbon thin line of the carbon thin line probe according to any one of the first to sixth aspects is formed into a carbon nanotube (CNT).

In an eighth aspect of the invention, a scanning probe microscope is constructed with using the carbon thin line probe according to any one of the first to seventh aspects to a cantilever probe.

In a ninth aspect of the invention, a micro-injector is constructed with using the carbon thin line probe according to any one of the first to seventh aspects to a probe.

BRIEF DESCRIPTION OF THE DRAWINGS

FIG. 3 shows a schematic sectional view of an SPM cantilever to which a carbon thin line probe according to the present embodiment is applied. FIG. 3 includes: 1, a support portion fabricated by processing a single-crystal silicon wafer; 2, a silicon-made lever portion extended from the support portion 1; 3, a silicon-made probe formed on a free end 4 side of lever portion 2; 5, a graphite film, i.e., a carbon compound serving as a supply source of the carbon thin line, forming a coat so as to cover the entire surface of the probe forming side of lever portion 2 and the entire portion of the probe 3. Also shown are: 7, a piece of carbon nanotube (CNT) thin line grownlformed at a probe terminal end portion 3a; and 6a, an internally contained metal consisting of a magnetic materials such as Fe, Ni, Co or an alloy of these metals internally contained at a terminal end portion of CNT thin line 7. Here CNT thin line 7 is formed into a tube. In other words, a hollow structure is formed along those portions of CNT thin line 7 other than the portion where the internally contained metal 6a consisting of a metal or alloy of the above metals is internally contained.

A brief description will now be given with reference to FIGS. 4A to 4C and FIG. 5 of the manufacturing method of an SPM cantilever where CNT thin line 7 internally containing Fe metal 6a as the metal or its alloy of a magnetic material is formed on the probe terminal end portion 3a.

Figure 1A:
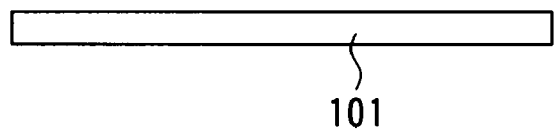
FIGS. 1A to 1D are manufacturing process drawings for explaining a manufacturing method of prior-art CNT having a metal ultrafine particle fixed at a terminal end portion thereof.
Figure 1B:
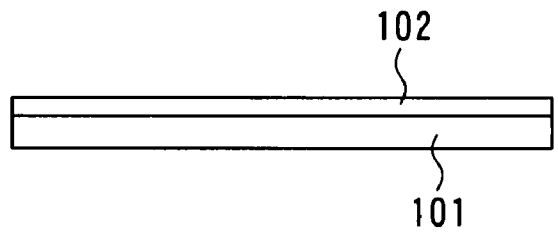
Figure 1C:
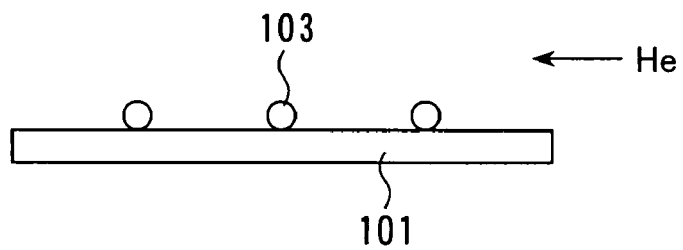
Figure 1D:
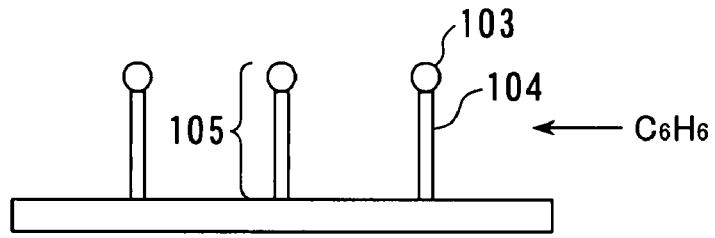
Figure 2:
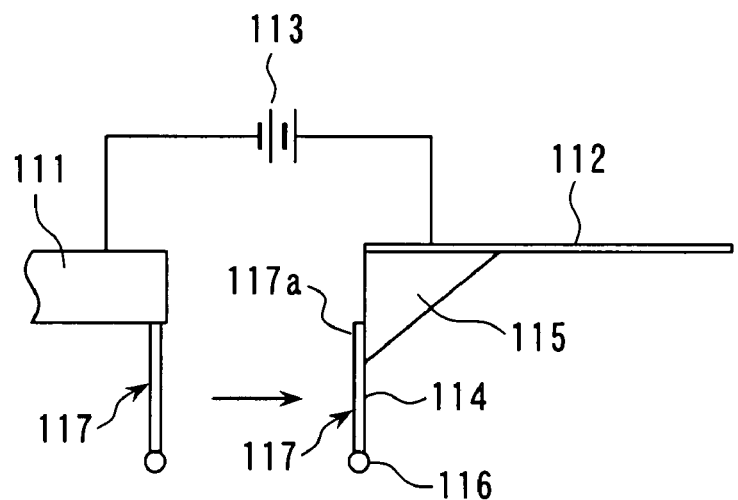
FIG. 2 illustrates a method for adhering and fixing to a probe terminal end portion of the AFM cantilever the prior-art CNT having a metal ultrafine particle fixed at a terminal portion thereof as shown in FIGS. 1A to 1D.
Figure 3:
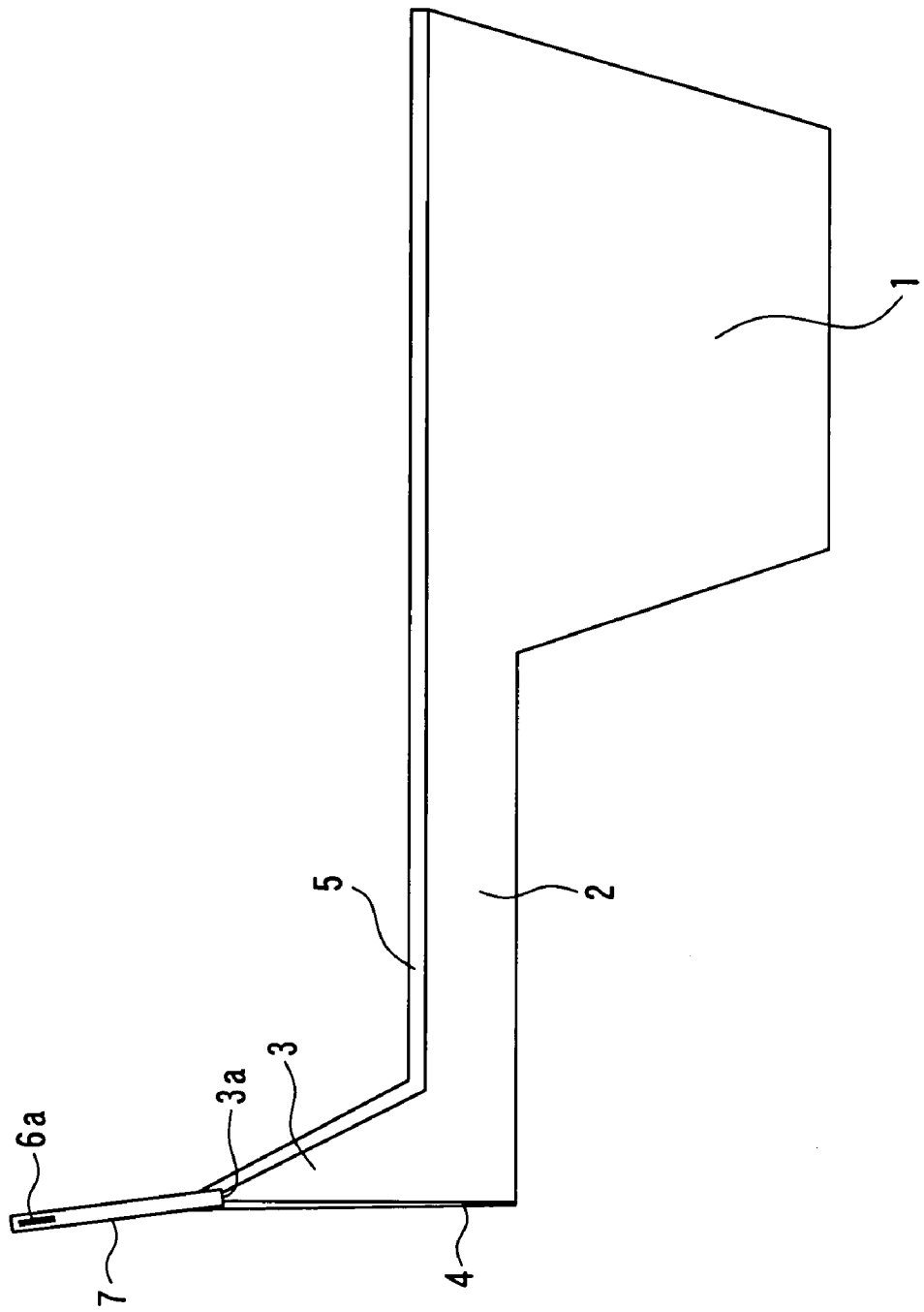
FIG. 3 is a schematic sectional view showing construction of an SPM cantilever having the carbon thin line probe according to an embodiment of the invention.
Figure 4A:
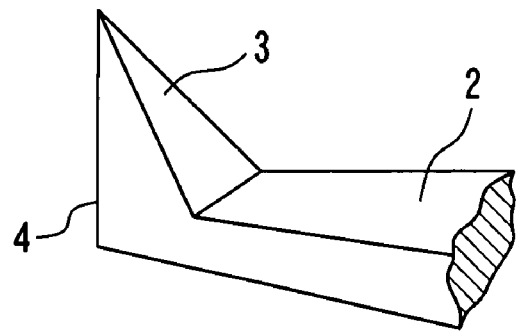
FIGS. 4A to 4C are manufacturing process drawings for explaining a manufacturing method of the SPM cantilever shown in FIG. 3.

First, a silicon-made cantilever as shown in FIG. 4A where the support portion (not shown), lever portion 2 and probe 3 are all fabricated by processing a silicon wafer is prepared. The probe 3 is in the form of a pyramid and preferably for example of a tetrahedral type triangular pyramid. This is because the probe terminal end portion is conspicuous as a projection for growing/forming CNT.

Figure 4B:
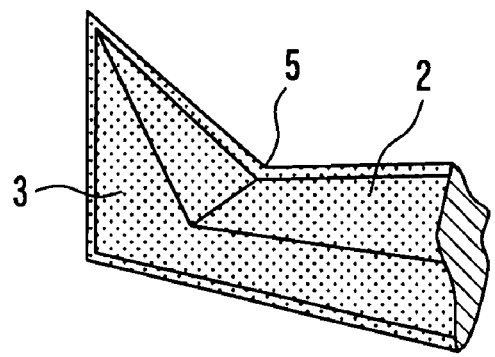

Next as shown in FIG. 4B, a graphite film 5 of a carbon material for example is formed to have a film thickness of several nm to several µm by means of sputtering or electron beam evaporation on the front side of lever portion 2 on which the probe 3 is formed and side surfaces of the probe 3. The graphite film 5 serves as a supply source of carbon when carbon nanofiber (CNF) thin line is to be formed, an equivalent effect being obtainable for a wide range of film thickness.

Next, a piece of noncrystalline carbon nanofiber (CNF) thin line 7a internally containing metal (Fe) in a selective manner at a probe terminal end portion of the cantilever is caused to grow while controlling its direction in an ultra-high vacuum apparatus.

Figure 5:
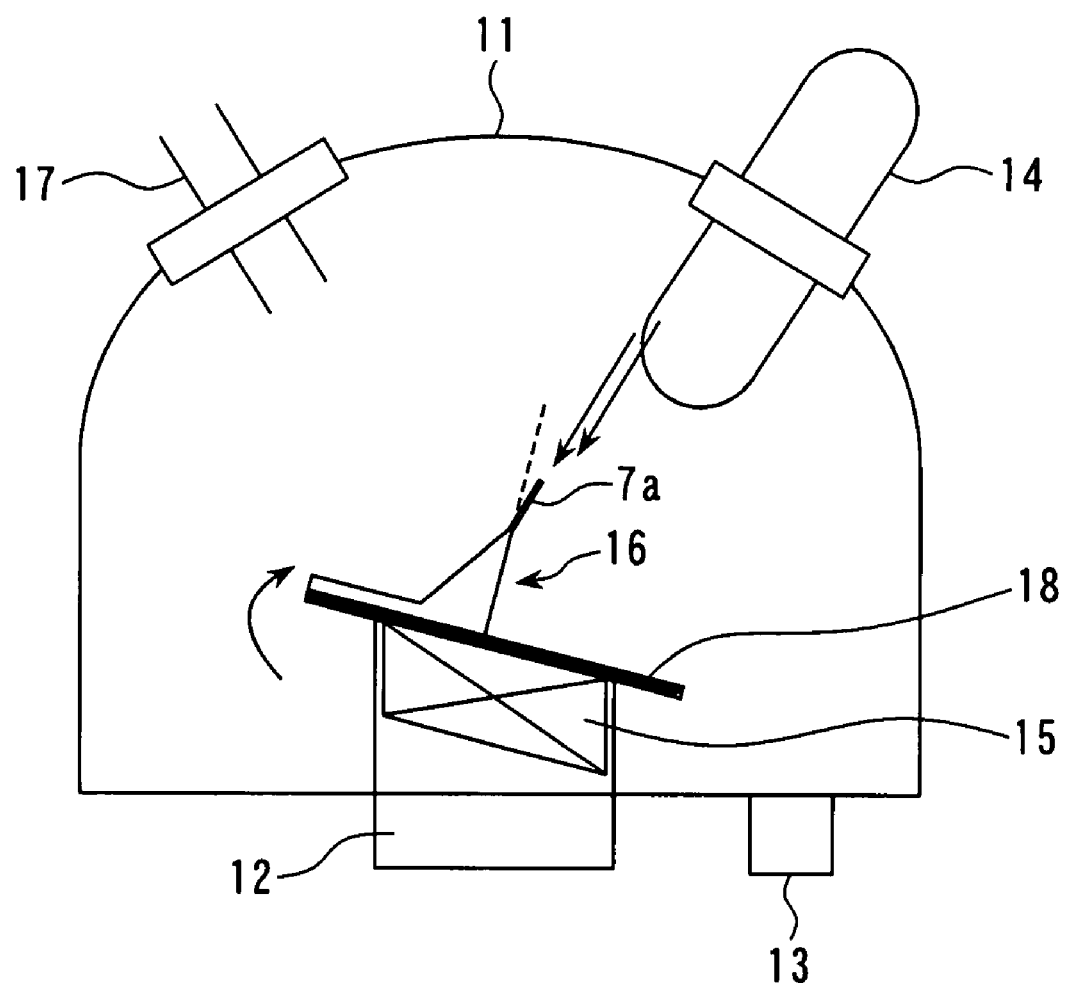
FIG. 5 shows the manner of growing/forming a CNF thin line using a ultra-high vacuum apparatus in the manufacturing process shown in FIGS. 4A to 4C.

Here, in growing CNF thin line 7a, as shown in FIG. 5, an ultra-high vacuum apparatus 11 is provided as having: a vacuum outlet 13; an ion gun 14 having a beam diameter of several mm to several-ten cm for irradiating a high-energy beam; a variable angle sample stage 18 having a heater section 15 for heating sample; a drive section 12 for controlling an angle of the sample stage 18; and a metal introducing entrance 17 for supplying a metal from the outside.

In thus constructed ultra-high vacuum apparatus 11, a cantilever 16 is placed on the stage 18 with making the stage 18 movable so that the ion gun 14 is parallel to the direction along which CNF thin line 7a is grown. At this time, the cantilever 16 is placed such that CNF thin line 7a is formed with an inclination of about 12° toward the free end of lever portion 2 with respect to the probe 3 which is formed vertically to the lever portion 2.

The reason for this is that, when the SPM cantilever is used as it is set for example to an SPM apparatus, the lever portion surface is generally set with an inclination of about 12° to bring back the reflected laser beam from the lever portion surface to normal on a photodetector. Thereby the scanning can be effected with keeping the terminal end of CNT thin line 7 to be described later always to a nearest position to the sample to be measured, making high-resolution measurements possible. Naturally, an angle other than 12° may be used as the above described inclination angle according to its use in forming CNT thin line 7 onto the probe while controlling the angle.

At the interior of such ultra-high vacuum apparatus 11, while an ion irradiation of 1 to 100 minutes at room temperature is being effected with setting a vacuum of the order of $10^{-2}$ to $10^{-8}$ Pa and preferably of $10^{-3}$ to $10^{-5}$ Pa, an acceleration voltage of 0.1 to 300 keV of argon ion serving as a noble gas ion source, an average ionic current density of the order of 2 µA/cm$^2$ to 10 mA/cm$^2$, and a sputter rate of ion beam of the order of 2 nm to 1 µm/min, Fe is supplied from the metal introducing entrance 17 by evaporating for example Fe(CO)$_6$ (ferrocene). A noncrystalline CNF thin line 7a of about 1 µm internally containing Fe at its base portion is thereby grown/formed at the probe terminal end portion. At this time, Fe atom to be supplied may be of a very small amount, and a quantity in atomic weight for example of equal to or less than 5% of CNF thin line 7a suffices.

While the growing of CNF thin line 7a at room temperature has been shown, it is also possible to effect the growth while heating it from room temperature to about 500 to 600° c. or cooling it from room temperature to−150° C. In the case of changing temperature at the time of ion beam irradiation in this manner, the growth rate of CNF thin line 7a can be controlled. Further, by changing the ionic current density and acceleration voltage of the ion beam, the sputter rate can be readily changed. Further, while one using argon ion as a noble gas ion source has been shown, helium ion, neon ion, or xenon ion may also be used, or it is possible to use a reactive gas ion sources such as nitrogen ion, oxygen ion, or an ion containing CH radical.

Next, it is heated at a temperature of about 700° C. for thirty minutes or more and preferably for about an hour in a vacuum of the order of $10^{-2}$ to $10^{-8}$ Pa. The noncrystalline CNF thin line 7a is thereby formed into a crystal and becomes a carbon nanotube (CNT) thin line 7 having a tubular crystal structure internally containing Fe metal (contained metal) 6a at its terminal end portion. Here, Fe metal (contained metal) located at a base portion of the noncrystalline CNF thin line 7a is moved toward the terminal end due to the heat treatment so that the back side of the moving of Fe metal (contained metal) 6a is formed into a tube and crystallized to become CNT thin line 7.

Figure 4C:
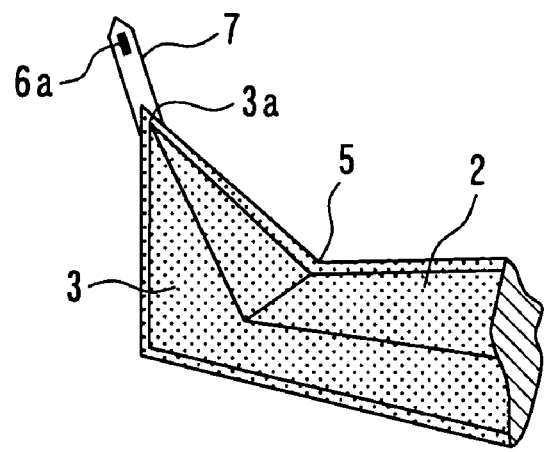

An SPM cantilever having a carbon thin line probe is complete as the above, in which CNT thin line 7 internally containing the contained metal 6a consisting of magnetic Fe metal at its terminal end is formed as shown in FIG. 4C at the terminal end portion 3a of the probe 3 of lever portion 2.

By thus causing a magnetic metal to be internally contained in CNT thin line of a carbon thin line probe, it is possible to readily form a CNT thin line probe which, at the same time of having magnetic characteristic, is firmly fixed to the projection-like terminal end portion (terminal end portion of probe) so as to be highly durable and reliable.

Further, when SPM cantilever having carbon thin line probe where CNT thin line internally containing metal is formed at a probe terminal end portion in this manner is mounted on SPM apparatus, the terminal end of the carbon thin line probe can be placed always vertical to a sample horizontal surface, and since the resulting probe is of high aspect ratio, an improved resolution can be expected at the time of SPM measurements. Further, since it is exceptionally hard as a probe and internally contains a magnetic metal within the CNT thin line, the magnetic metal does not come off unlike the ultrafine particle of the prior-art example which is fixed to CNT thin line. A magnetic characteristic of sample can then be measured at high resolution with high durability so that it is possibly used as a cantilever of magnetic force microscope (MFM). Furthermore, this leads to a cost reduction, since the carbon thin line probe can be fabricated with forming only one piece of metal-contained CNT thin line at a terminal end portion in a well controlled and reproducible manner through batch fabrication.

Further, since a carbon-type material is formed only at the probe terminal end portion while the lever portion including the probe is formed only of silicon which has conventionally been used, its mechanical characteristic is stable. Furthermore, since CNT thin line is grown with having substantially the same thickness, length, and direction, a carbon thin line probe having a high aspect ratio can be achieved. Reproducible and stable high-resolution measurements are thereby possible even of a sample having large surface irregularities. Accordingly, a highly reliable SPM cantilever can be achieved.

It should be noted that, while the supplying of metal ion at the same time of an ion beam irradiation has been shown in the present embodiment as the method for causing a metal to be internally contained in CNF thin line, it is also possible to perform an ion beam irradiation after previously depositing the metal to be contained at a probe terminal end portion of cantilever.

Figure 6A:
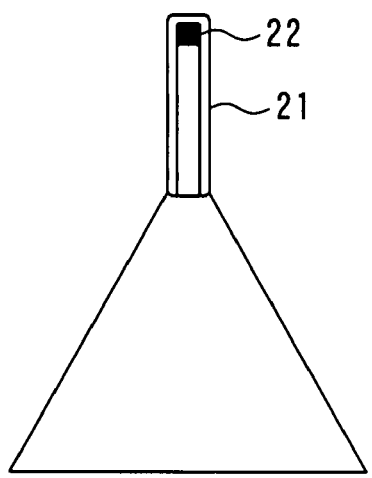
FIGS. 6A to 6E each are a schematic enlarged sectional view of the carbon thin line probe according to the carbon thin line probe shown in FIG. 3 and modifications thereof. Description of the Preferred Embodiment An embodiment of the carbon thin line probe according to the invention will now be described with reference to the drawings.
Figure 6B:
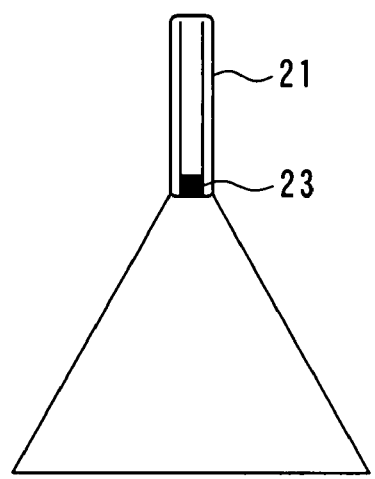

While an explanation has been made in the present embodiment with respect to CNT thin line internally containing Fe metal at its terminal end, a magnetic metals such as Ni or Co or an alloy containing these other than Fe metal may also be used as the metals to be contained. Further, the manner of internally containing the metal to be contained within CNT thin line may be changed by the types and supply amount of metal. Specifically, when a very small amount of Ni is supplied, Ni metal 22 is internally contained as shown in FIG. 6A at a terminal end portion of CNT thin line 21 similarly to the case of Fe. On the other hand, when a very small amount of Co is supplied, Co metal 23 is internally contained as shown in FIG. 6B at a base portion of CNT thin line 21. The reason for this is that Co remains at the base portion of CNT thin line 21 as it is firmly rooted into silicon of the probe terminal end portion whereby a tubular CNT is formed toward the terminal end.

Figure 6C:
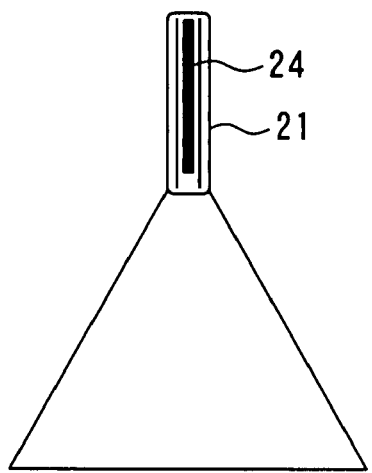
Figure 6D:
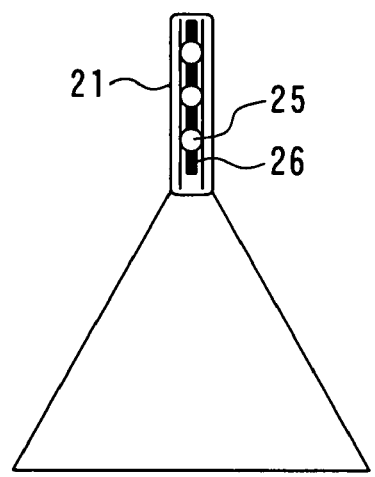
Figure 6E:
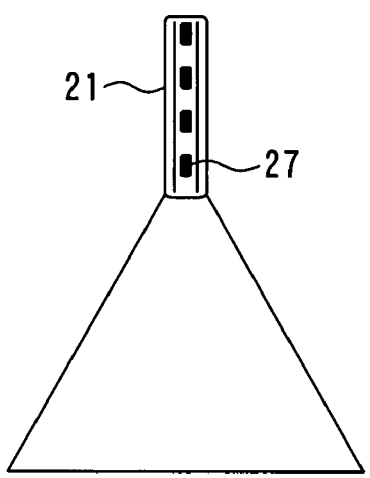

Further, when a metal having an atomic density of about ¼ of CNF thin line to be formed on the probe terminal end portion is supplied, a contained metal 24 is internally contained uniformly through the entire portion of CNT thin line 21 as shown in FIG. 6C. Furthermore, if, during the growing/forming of CNF thin line, a first metal is initially supplied and a second and further metals are supplied in the middle, a plurality of different metals 25 and 26 are internally contained within CNT thin line 21 in the form of a multilayer structure as shown in FIG. 6D. Further, when only one metal is intermittently supplied, metal 27 is internally contained in a scattered manner as shown in FIG. 6E. A plurality of metals may also be used at this time, and, in such a case, a plurality of different types of metals are internally contained in a scattered manner. It should be noted that, also in the case where the metal is internally contained at the terminal end portion or base portion of CNT thin line as shown in FIGS. 6A and 6B, it is possible to cause it to be internally contained not only in a monolithic manner as shown in the figures but also in a scattered manner at the terminal end portion or base end portion.

Further, use of magnetic metal such as Fe, Ni, or Co as the internally contained metal has been shown in the above description, it is naturally also possible to use a high melting point metal, such as Ti, Mo, or W, as the internally contained metal. When these high melting point metals are used, though a magnetic characteristic cannot be imparted unlike the magnetic metals, it is much more easier to form CNT thin line internally containing metal as compared to the case where a magnetic metal is used.

Furthermore, while the forming of a graphite film over the entire surface on the probe forming side of lever portion and over the entire portion of the probe as supply source for forming CNF thin line has been shown in the present embodiment, it is also possible to form a graphite film only at a probe terminal end portion on which CNF thin line is to be grown/formed. In other words, it suffices to form a graphite film only at the portion where CNF thin line is to be grown/formed, i.e. in this case a projecting portion of the probe terminal end portion.

The supply source for forming CNF thin line is not limited to a graphite film, and those compounds containing carbon elements such as silicon carbide (SiC), glassy carbon (g-C), diamond-like carbon (DLC), amorphous carbon (a-C), titanium carbide (TiC), tungsten carbide (WC), chromium carbide (CrC), vanadium carbide (VC), or niobium carbide (NbC), may similarly be used as the supply source. Furthermore, the film forming method of carbon compound serving as the supply source for forming CNF thin line is not limited to sputtering or electron beam vapor deposition, and it is naturally also possible to use CVD or other vapor deposition methods.

On the other hand, since the probe itself becomes a supply source of carbon if at least the probe of cantilever is fabricated from a carbon compound, CNF thin line can be readily grown and formed at the probe terminal end portion without requiring to form a film of an additional carbon compound.

The shape of the probe of SPM cantilever in the present embodiment has been shown but is not limited to one using a tetrahedral form. Naturally pyramidal or polygonal pyramidal probes, or any projecting probes such as of conical probes may similarly be used as the shape of the probe.

While an example of applying the carbon thin line probe to the probe of SPM cantilever has been shown in the present embodiment, it is naturally possible to apply the carbon thin line probe according to the invention not only to SPM cantilever but also to a probe of micro-injector which is used for example when a gene is introduced into a cell. The carbon thin line probe according to the embodiment applied to SPM cantilever may be applied as it is to the fundamental construction of micro-injector probe, since it is constituted by a support portion, lever portion and probe portion similarly as an SPM cantilever. Further, a micro-injector probe, unlike SPM cantilever, is not necessarily required to have a lever portion. Also in the case of such construction, the carbon thin line probe according to the invention can be used equivalently as a micro-injector probe.

As has been described by way of the above embodiments, it is possible according to the invention to readily provide CNT thin line probe having high aspect ratio and high durability and reliability with internally containing a metal. It is also possible to impart a magnetic characteristic by suitably selecting the metal to be contained. Furthermore, CNT thin line probe can be manufactured by a manufacturing method which is simple and capable of batch processing. Moreover, CNT thin line probe can be widely applied to the probes of SPM cantilever, micro-injector, etc.

The advantages of each aspect of the invention are as follows. According to the first aspect of the invention, a carbon thin line probe having high durability and reliability can be achieved. According to the second to fifth aspects of the invention, a carbon thin line probe internally containing a metal can be achieved in a manner suitable for its use or characteristic. According to the sixth aspect of the invention, a carbon thin line probe with an imparted magnetic characteristic can be achieved. According to the seventh aspect of the invention, a carbon thin line probe having additional high durability and reliability can be achieved. According to the eighth and ninth aspects of the invention, an SPM cantilever or micro-injector can be achieved as having a probe which makes high-resolution measurements possible and at the same time is highly reliable.

What is claimed is:

1. A carbon thin line probe comprising a carbon thin line selectively and integrally formed at and with a projected terminal end portion thereof by means of irradiation of an energy beam, onto an entire surface of a probe base portion including the projected terminal end portion on the surface of which a carbon-system material film is previously formed, wherein said carbon thin line internally contains a metal, wherein said internally contained metal is formed through the entire portion of said carbon thin line such that said internally contained metal uniformly fills the entire portion of said carbon thin line.

* * * * *